United States Patent [19]

Chen

[11] Patent Number: 4,728,320

[45] Date of Patent: Mar. 1, 1988

[54] SYRINGE CAP WITH HAMMER

[76] Inventor: Chang-Cheng Chen, No. 211, Sec. 2, Chiu-Ru Rd., Chiu-Ru Hsiang, Pingtung Hsien, Taiwan

[21] Appl. No.: 42,222

[22] Filed: Apr. 17, 1987

[51] Int. Cl.$^4$ .............................................. A61M 5/00
[52] U.S. Cl. ...................................... 604/110; 604/192
[58] Field of Search ............... 604/110, 187, 192, 197, 604/198, 263

[56] References Cited

U.S. PATENT DOCUMENTS

| | | | |
|---|---|---|---|
| 3,796,359 | 3/1974 | Dick | 604/110 |
| 3,893,608 | 7/1975 | Koenig | 604/110 |
| 4,266,544 | 5/1981 | Wardlaw | 604/110 |
| 4,634,428 | 1/1987 | Cuu | 604/110 |

Primary Examiner—John D. Yasko
Attorney, Agent, or Firm—Lowe, Price, LeBlanc, Becker & Shur

[57] ABSTRACT

A syringe cap includes a hollow cap body and a hammer body fitted in a fitting body which in turn is fitted slideably in an end of the cap body for telescoping movement. The hammer body has a hitting end with a concaved surface facing a closed end of the fitting body which can be pierced by the needle. The needle bent by the concaved surface can engage permanently with the closed end so that the hammer body and the fitting body will never separate from the cap body.

4 Claims, 5 Drawing Figures

SYRINGE CAP WITH HAMMER

BACKGROUND OF THE INVENTION

The present invention relates to a syringe cap for capping a used syringe and, more particularly, to a syringe cap with a hammer means for destroying a needle of a syringe.

Syringes of varying materials are well-known in the art of medical treatment, such as, those made of glass or plastic. Plastic syringes are convenient to use since they are cheap and can be discarded after use. However, proper disposal of used syringes remains to be a problem because the needles of the used syringes may injure an individual. U.S. Pat. No. 4,634,428 to Cwo-Liang Cuu discloses a cover for a used syringe which includes a hollow cover body to be mounted on and encase the needle of the syringe and a telescopic needle destroying cap mounted slideably to one end of the cover body. When an impact force is applied to the cap, the cap destroys or bends the needle and then retain the bend needle in a bulbous lip at the interior surface of the cap. Although the cap can enclose the bend needle permanently, it can not be manufactured easily.

SUMMARY OF THE INVENTION

It is therefore a main object of the present invention to provide a syringe cap of simple construction which can be manufactured easily for destroying a syringe needle and enclosing the destroyed needle for ever so that the needle will never cause infection to an individual.

The present invention provides a syringe cap which comprises a hollow cap body having a surrounding wall for encasing a needle of a syringe, a first open end to be mounted on the syringe and a second open end to extend beyond the needle, a hammer body having a hitting end with a concaved surface and an opposite end, and a fitting member having an open end, an opposite closed end that can be pierced by the needle, and a cavity opening at the open end of the fitting member and closed by said closed end.

The fitting member is fitted slideably in the second open end of the cap body, and the manner body is received in the cavity. The concaved surface faces the closed end of the fitting member and strike the needle which pierces the closed end when an impact force is applied on the hammer member. The needle bent thereby engages with the closed end, Preferably, the deepest portion of the concaved surface is offset from the axis of the hammer body so as to cause the needle to bend along the contour of the concaved surface.

The exemplary preferred embodiment will be described in detail with reference to the following drawings, in which:

DETAILED DESCRIPTION OF THE PREFERRED EMBODIMENT

Figure 1:
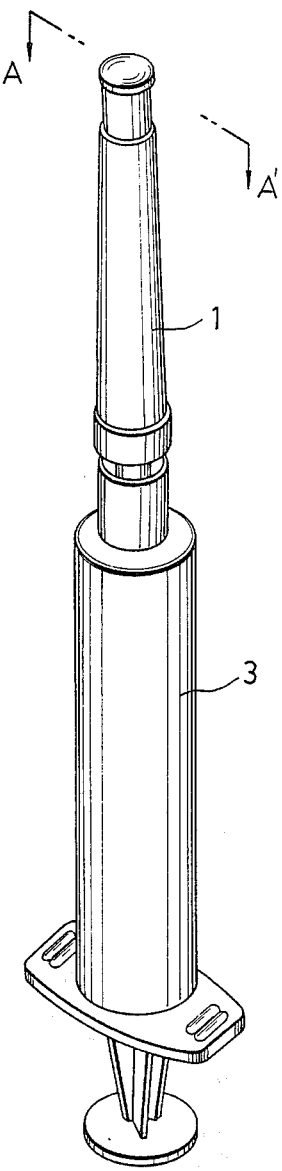
FIG. 1 is a perspective view of a syringe incorporating a syringe cap of the invention.
Figure 2:
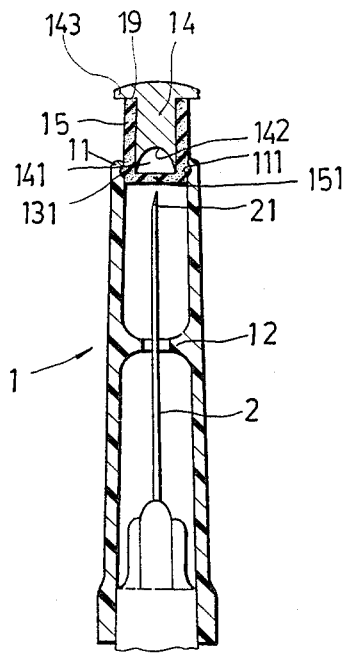
FIG. 2 is a sectional view taken along line A—A' of FIG. 1.
Figure 3:
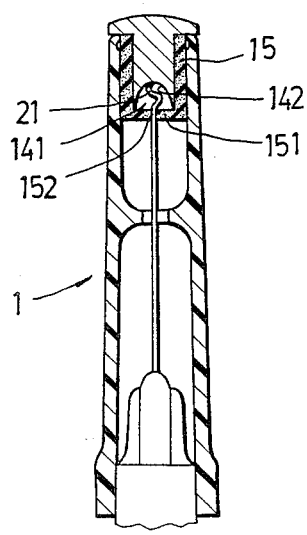
FIG. 3 is a sectional view showing that the needle is bent.

Referring to FIGS. 1 to 3, a substantially cylindrical hollow cap body 1 is shown, encasing a needle 2 of a syringe 3 and having one open end thereof mounted on the syringe 3. Another open end 11 of the syringe 3 extends beyond the end of the needle 2. Inside the hollow cap body 1 is an annular projection 12 extending inwardly from the inner side of the wall of the cap body 1 to restrict the lateral movement of the needle 2 or to center the needle 2 in the cap body 1.

A hammer body 14 is provided at the top open end 11 of the cap body 1, having a hitting end provided with a concaved surface 141 and an opposite flanged end 143 with a radially extending flange. The hammer body 14 is connected to the cap body 1 by means of a fitting member 15.

The fitting member 15 is a cylindrical body made of a plastic material and has a cylindrical cavity closed by a closed end 151 which can be pierced by the needle. The cavity opens at an opposite open end 19 of the fitting member 15 and the hammer body 14 is fitted in the cavity. A portion of the fitting member 15 adjacent to the closed end 151 is fitted slideably in the top open end of the cap body 1 for telescoping movement relative to the cap body, an annular projection 131 of the fitting member 15 being engaging releaseably with an annular recess 111 of the cap body 1.

The concaved surface 141 has a cross-section substantially conforming to a parabola and faces the closed end 20 of the fitting member 20. The deepest portion 141 of the concaved surface 141 is substantially at the central portion of the hammer body 14 to strike the needle of the syringe directly.

Figure 4:
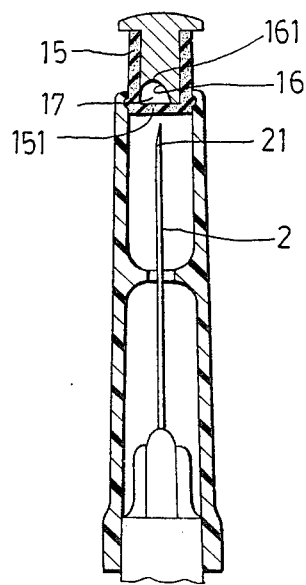
FIG. 4 is also a sectional view of a syringe cap of FIG. 1 but with an alternative concaved surface.
Figure 5:
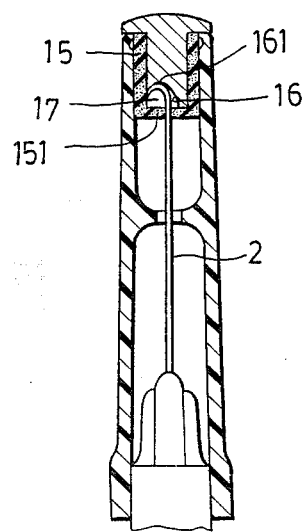
FIG. 5 is a sectional view showing that the needle is bent by said alternative concaved surface.

FIGS. 4 and 5 show an alternative concaved surface 17 of the hammer body 14. The concaved surface 17 also has a cross-section substantially conforming to a parabola facing the closed end 151 of the fitting member 15. But, the vertex portion 161 of said concaved surface is offset from the axis of the hammer body 14. As such, the end 21 of the needle 2 which will pierce the closed end 151 of the fitting member 15 at 152 towards the concaved surface upon impact will not be struck directly by the vertex portion 161. The curved portion 16 of the concaved surface 17 has a gradually varying inclinations with respect to the axis of the hammer body 14 and extends adjacent said axis from the end face of the fitting body 15 to the vertex portion 161 of the concaved surface 17 to cause the needle 2 to bend gradually towards the vertex portion 161 and then to an opposite curved portion.

When a used syringe is capped with the syringe cap 1 of the invention, and an impact is applied on the hammer body 14 such as by holding the cap body 1 and then hitting the hammer body 14 against a hard surface, the hammer body 14 together with the fitting member is pushed entirely into the cap body 1 expect for the flanged end 143 of the hammer body 14 engaging with the end of the cap body 1 at the exterior of the cap body. In this situation, the end of the needle 2 pierces the closed end 151 of the fitting member 15 and forms a bend conforming to the contour of the concaved surface 17. The bent end of the needle 2 will never escape from the fitting member 15 due to its engagement with the closed end 151 and, accordingly, the hammer body 14 and the fitting member 15 will seal off permanently the cap body 1. As the result, the needle of the syringe will never injure an individual.

With the invention thus explained, it is apparent that various modifications and variations can be made without departing from the scope of the invention. It is therefore intended that the invention be limited as indicated in the appended claims.

What I claim is:

1. A syringe cap comprising:
   a hollow cap body having a surrounding wall for encasing a needle of a syringe, a first open end to be mounted on the syringe and a second open end to extend beyond the needle;
   a hammer body having a hitting end with a concaved surface and an opposite end; and
   a fitting member which has an open end, an opposite closed end that can be pierced by the needle and a cavity opening at said open end of said fitting member and closed by said closed end;
   said fitting member being fitted slideably in said second open end of said cap body for telescoping movement between an extended position and a retracted position, said hammer body being held in said cavity, said concaved surface being facing said closed end, said fitting member being forced to move to said retracted position when an impact force is applied and said caoncaved surface hitting the needle which pierces said closed end.

2. A syringe cap as claimed in claim 1, wherein said concaved surface has a deepest portion offset from an axis of said hammer body and a bending surface of gradually varying inclinations relative to said axis to cause the needle to bend along the contour of said concaved surface.

3. A syringe cap as claimed in claim 2, wherein said concaved surface has a cross-section conforming to the contour of a parabola.

4. A syringe cap as claimed in claim 1, wherein said surrounding wall is substantially cylindrical and has an annular projection extending inwardly from the surrounding wall to prevent the needle from lateral movement.

* * * * *